United States Patent
Day

(10) Patent No.: US 9,939,383 B2
(45) Date of Patent: Apr. 10, 2018

(54) ANALYZER ALIGNMENT, SAMPLE DETECTION, LOCALIZATION, AND FOCUSING METHOD AND SYSTEM

(71) Applicant: SciAps, Inc., Woburn, MA (US)

(72) Inventor: David R. Day, Boxford, MA (US)

(73) Assignee: SciAps, Inc., Woburn, MA (US)

( * ) Notice: Subject to any disclaimer, the term of this patent is extended or adjusted under 35 U.S.C. 154(b) by 17 days.

(21) Appl. No.: 15/016,489

(22) Filed: Feb. 5, 2016

(65) Prior Publication Data

US 2017/0227469 A1 Aug. 10, 2017

(51) Int. Cl.
  *G01J 3/30* (2006.01)
  *G01N 21/71* (2006.01)
  *G01J 3/443* (2006.01)

(52) U.S. Cl.
  CPC ............ *G01N 21/718* (2013.01); *G01J 3/443* (2013.01)

(58) Field of Classification Search
  CPC .... G01N 21/718; G01J 3/0272; G01J 3/2823; G01J 3/443; G01J 3/0204
  See application file for complete search history.

(56) References Cited

U.S. PATENT DOCUMENTS

| 3,760,144 | A | 9/1973 | Herzberger |
| 4,358,659 | A | 11/1982 | Spohnheimer |
| 4,770,486 | A | 9/1988 | Wang et al. |
| 5,473,162 | A | 12/1995 | Busch et al. |
| 5,520,679 | A | 5/1996 | Lin |
| 6,006,140 | A | 12/1999 | Carter |
| 6,077,386 | A | 6/2000 | Smith, Jr. et al. |
| 6,104,945 | A * | 8/2000 | Modell ............ A61B 1/00059 250/461.2 |
| 6,124,928 | A * | 9/2000 | Slater ..................... G01J 3/44 356/301 |
| 6,355,908 | B1 | 3/2002 | Tatah et al. |
| 6,568,418 | B1 | 5/2003 | Hope et al. |

(Continued)

FOREIGN PATENT DOCUMENTS

WO WO 2012/040769 A1 4/2012
WO WO 2012/135961 A1 10/2012

(Continued)

OTHER PUBLICATIONS

Written Opinion of the International Searching Authority for PCT Application No. PCT/US2014/11961 dated May 8, 2014 (six (6) pages).

(Continued)

*Primary Examiner* — Kara E Geisel
*Assistant Examiner* — Maurice Smith
(74) *Attorney, Agent, or Firm* — Iandiorio Teska & Coleman, LLP

(57) ABSTRACT

An analysis (e.g., LIBS) system includes a source of radiation, an optical emission path for the radiation from the source of radiation to a sample, and an optical detection path for photons emitted by the sample. A detector fiber bundle transmits photons to the spectrometer subsystem. At least one fiber of the fiber bundle is connected to an illumination source (e.g., an LED) for directing light via at least a portion of the detection path in a reverse direction to the sample for aligning, sample presence detection, localizing, and/or focusing based on analysis of the resulting illumination spot on the sample.

4 Claims, 11 Drawing Sheets

(56) References Cited

U.S. PATENT DOCUMENTS

| | | | |
|---|---|---|---|
| 6,801,595 B2 | 10/2004 | Grodzins et al. | |
| 7,233,643 B2 | 6/2007 | Sipilä et al. | |
| 7,394,537 B1 | 7/2008 | Lindfors et al. | |
| 7,676,061 B2 | 3/2010 | Harrison et al. | |
| 7,821,634 B2 | 10/2010 | Dillon et al. | |
| 8,184,287 B2 | 5/2012 | Hamilton et al. | |
| 8,199,321 B2 | 6/2012 | Yoo et al. | |
| 8,436,991 B2 | 5/2013 | Senac | |
| 8,576,382 B2 | 11/2013 | LaValley et al. | |
| 8,655,807 B2 | 2/2014 | Multari et al. | |
| 2001/0015801 A1 | 8/2001 | Hirose et al. | |
| 2002/0009814 A1 | 1/2002 | Usui et al. | |
| 2002/0174325 A1 | 11/2002 | Iwanaga | |
| 2003/0010907 A1 | 1/2003 | Hayek et al. | |
| 2003/0174325 A1 | 9/2003 | Zhang et al. | |
| 2003/0234928 A1 | 12/2003 | Lucas et al. | |
| 2004/0183010 A1 | 9/2004 | Reilly et al. | |
| 2005/0032459 A1 | 2/2005 | Surana et al. | |
| 2005/0056628 A1 | 3/2005 | Hu | |
| 2005/0068524 A1* | 3/2005 | Wu | G01J 3/02 356/316 |
| 2005/0142260 A1 | 6/2005 | Chen et al. | |
| 2005/0236563 A1 | 10/2005 | Busch et al. | |
| 2005/0248758 A1 | 11/2005 | Carron et al. | |
| 2006/0100676 A1 | 5/2006 | Walmsley | |
| 2006/0262302 A1 | 11/2006 | Eklin | |
| 2007/0187632 A1 | 8/2007 | Igarashi | |
| 2007/0195311 A1 | 8/2007 | Morgan | |
| 2007/0202613 A1 | 8/2007 | Usui | |
| 2007/0265783 A1 | 11/2007 | Mound | |
| 2007/0296967 A1* | 12/2007 | Gupta | G01J 3/2889 356/318 |
| 2008/0151241 A1 | 6/2008 | Lindfors et al. | |
| 2008/0165344 A1 | 7/2008 | Treado et al. | |
| 2008/0205755 A1 | 8/2008 | Jackson | |
| 2008/0259330 A1 | 10/2008 | Dillon et al. | |
| 2009/0007933 A1* | 1/2009 | Thomas | B08B 7/0042 134/1 |
| 2009/0025761 A1 | 1/2009 | Matsumoto | |
| 2009/0057422 A1 | 3/2009 | Dugas et al. | |
| 2009/0103082 A1 | 4/2009 | Black et al. | |
| 2010/0197116 A1 | 8/2010 | Shah et al. | |
| 2011/0100967 A1* | 5/2011 | Yoo | B23K 26/032 219/121.73 |
| 2011/0246145 A1* | 10/2011 | Multari | G01J 3/28 703/2 |
| 2011/0315661 A1 | 12/2011 | Morisawa | |
| 2012/0029836 A1 | 2/2012 | Hermann | |
| 2012/0044488 A1 | 2/2012 | Senac | |
| 2012/0085366 A1 | 4/2012 | Hirota | |
| 2012/0162642 A1 | 6/2012 | Watson et al. | |
| 2012/0206722 A1 | 8/2012 | Grigoropoulos et al. | |
| 2012/0236303 A1 | 9/2012 | Marple et al. | |
| 2012/0268743 A1 | 10/2012 | Wang et al. | |
| 2012/0314214 A1 | 12/2012 | Alexander et al. | |
| 2013/0016349 A1 | 1/2013 | Effenberger, Jr. et al. | |
| 2013/0271761 A1 | 10/2013 | Rutberg et al. | |
| 2013/0342902 A1 | 12/2013 | Krueger | |
| 2014/0022531 A1 | 1/2014 | Sackett | |
| 2014/0022532 A1 | 1/2014 | Sackett | |
| 2014/0125965 A1 | 5/2014 | Nagil | |
| 2014/0202490 A1 | 7/2014 | Day | |
| 2014/0204375 A1 | 7/2014 | Day | |
| 2014/0204376 A1 | 7/2014 | Day | |
| 2014/0204377 A1 | 7/2014 | Day et al. | |
| 2014/0204378 A1 | 7/2014 | Day | |
| 2015/0346103 A1* | 12/2015 | Wang | G01N 21/718 356/318 |
| 2016/0084757 A1* | 3/2016 | Miron | G01N 21/39 356/437 |
| 2016/0252398 A1 | 9/2016 | Day et al. | |

FOREIGN PATENT DOCUMENTS

| | | |
|---|---|---|
| WO | WO 2013/083950 A1 | 6/2013 |
| WO | WO 2015/057784 | 4/2015 |
| WO | WO 2015/057784 A1 | 4/2015 |

OTHER PUBLICATIONS

Written Opinion of the International Searching Authority for PCT Application No. PCT/US2014/11863 dated May 13, 2014 (nine (9) pages).

Written Opinion of the International Searching Authority for PCT Application No. PCT/US2014/12060 dated Jan. 27, 2015 (five (5) pages).

Written Opinion of the International Searching Authority for PCT Application No. PCT/US2014/016188 dated Feb. 2, 2015 (eight (8) pages).

Fisher et al., "Temporal Gating for the Optimization of Laser-Induced Breakdown Spectroscopy Detection and Analysis of Toxic Metals", Applied Spectroscopy, 55, 10, 2001, pp. 1312-1319.

Thorlabs, "Off-Axis Parabolic Mirrors With Holes Parallel to Collimated Beam", http://www.thorlabs.us/newgrouppage9.cfm?objectgroup_id=8172, Aug. 13, 2015, 2 pages.

Thorlabs, "Off-Axis Parabolic Mirrors With Holes Parallel to Focused Beam", http://www.thorlabs.us/newgrouppage9.cfm?objectgroup_id=7197, Aug. 12, 2015, 3 pages.

* cited by examiner

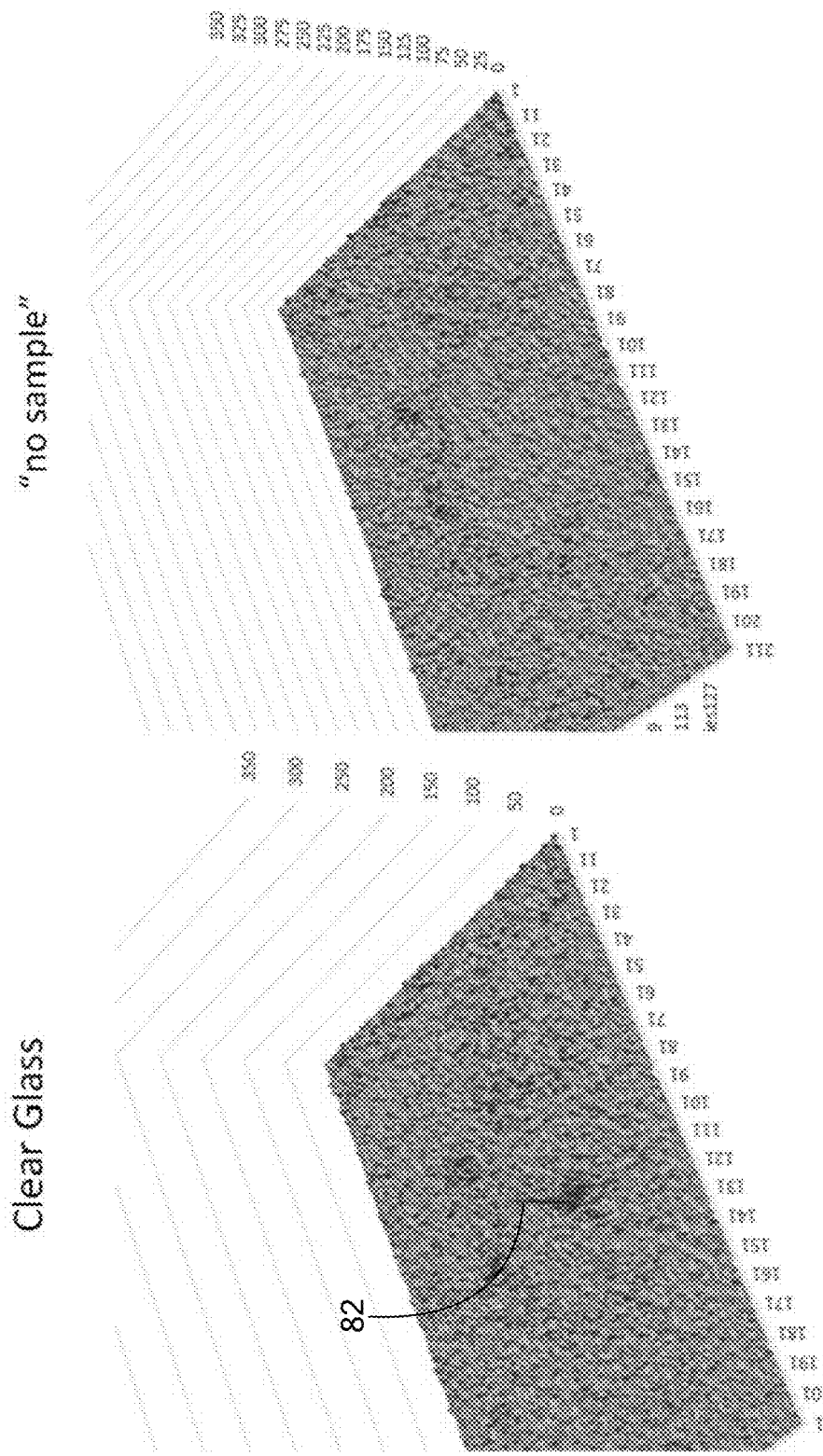

ANALYZER ALIGNMENT, SAMPLE DETECTION, LOCALIZATION, AND FOCUSING METHOD AND SYSTEM

FIELD OF THE INVENTION

The subject invention relates to spectroscopic instruments.

BACKGROUND OF THE INVENTION

Laser induced break down spectroscopy (LIBS) devices are known and used to detect the elemental concentration of elements with some accuracy. These devices typically include a high powered laser that sufficiently heats a portion of the sample to produce a plasma. As the plasma cools, eventually the electrons return to their ground states. In the process, photons are emitted at wavelengths unique to the specific elements comprising the sample. The photon detection and subsequent measurement of elemental concentrations are similar to spark optical emission spectroscopy (OES). Examples of LIBS devices are the LIBS SCAN 25 from Applied Photonics, the LIBS25000 from Ocean Optics, and the RT 100 from Applied Spectra. See also Nos. US 2012/0044488 and WO 2013/083950 (PCT/GB2012/000892) incorporated herein by this reference.

Portable, laser based Raman spectrometers can be used to determine the molecular compositions present in a sample. These devices are configured to collect Raman spectra from a given sample. They then compare the acquired spectra to a library of spectra of pure compounds. From the comparisons, the devices then determine the major compounds present in the sample. The process of determining what combination of pure compounds spectra in published libraries yield the measured spectrum of an unknown mixture is called chemometrics. There are several commercially available portable devices utilizing Raman technology including those manufactured by Thermo Fisher Scientific, Delta Nu and B&W Tek.

SUMMARY OF THE INVENTION

U.S. patent application Ser. No. 14/874,726 by the assignee hereof and incorporated herein by this reference discusses a handheld LIBS analyzer with a multi-branch fiber optic bundle having a common end positioned to receive plasma radiation generated via a laser beam directed to the sample. One or more branches of the fiber optic bundle are connected to individual spectrometers.

It can be difficult to properly align the fiber bundle common end during manufacturing of the handheld LIBS laser so that the focus of the detection path is coincident with laser excitation and the resulting plasma. Also, U.S. patent application Ser. Nos. 14/800,888 and 14/632,419 also by the assignee hereof and incorporated herein by this reference disclose methods to determine if a sample is present at the nose of the handheld LIBS analyzer in order to prevent the laser from being fired into the air. Additional techniques for detecting the presence of a sample may be desirable. Focusing the laser beam onto the sample is disclosed in U.S. patent application Ser. No. 13/746,110 by the assignee hereof and incorporated herein by this reference and in previously referenced U.S. application Ser. No. 14/874,726. Additional laser beam focusing techniques may be desirable.

In one example, the invention includes using at least one fiber optic of a fiber bundle to irradiate the sample with light via the detection and emission paths. A spot of light on the sample may be imaged and/or analyzed in order to perform alignment functions, sample presence detection functions, in order to localize the laser beam on a very specific sample location, and/or to focus the laser beam onto the sample.

Featured is an analysis method comprising directing radiation along a laser emission path to a sample, directing photons emitted by the sample along a detection path, and directing light from an illumination source via at least a portion of the detection path in a reverse direction to the sample creating an illumination spot thereon. By analyzing the illumination spot, several functions can be carried out: alignment, sample presence detection, localizing and/or focusing.

Analyzing the illumination spot on the sample may include imaging the illumination spot on the sample and/or employing a spectrometer. In one design, the detection path includes a fiber bundle having a common end located to receive photons emitted by the sample for directing the photons to one or more spectrometers. A fiber of this fiber bundle is coupled to the illumination source. Aligning may include adjusting the position of the detection fiber bundle common end based on the illumination spot. A laser beam may be used to create a mark on the sample and aligning includes adjusting the position of the detection fiber bundle common end until the illumination spot is concentric with the mark. Aligning may further include focusing the laser beam on the sample and adjusting the position of the fiber bundle common end until the size of the illumination spot is minimized. The sample may be a tape and the mark may be a hole created through the tape or the sample may be a substrate and the hole is a crater created in the substrate.

Detecting the presence of a sample may include energizing the illumination source and analyzing any light reflected off the sample. This method may further include de-energizing the illumination source and again analyzing any light reflected off the sample. Then, light reflected off the sample when the illumination source is de-energized is subtracted from the light reflected off the sample when the illumination source is energized. Analyzing radiation reflected off the sample may include imaging the sample or analyzing radiation reflected off the sample may include using a spectrometer subsystem to analyze radiation present along the detection path. Preferably, the method further includes inhibiting any radiation from proceeding along the optical emission path if the analysis indicates a sample is not present.

In one design, the emission path and the detection path both include an adjustable focusing lens. Localizing may include energizing the illumination source to create an illumination spot at a location on the sample and moving the illumination spot to a desired location on the sample by moving the sample and/or by using the adjustable focusing lens. Focusing may include energizing the illumination source to create an illumination spot on the sample and adjusting the focusing lens along the optical axis until the illumination spot size is minimized. Focusing may include imaging the illumination spot on the sample. Alternatively, focusing includes directing reflected radiation from the illumination spot on the sample via the detection path to a spectrometer subsystem and analyzing the brightness of the illumination spot.

Also featured is an analysis system comprising a source of radiation, an optical emission path for the radiation from the source of radiation to a sample, an optical detection path for photons emitted by the sample, a spectrometer subsystem for analyzing the photons, and a detector fiber bundle optically coupled to the optical detection path for transmitting the photons to the spectrometer subsystem.

At least one fiber of the fiber bundle connected to an illumination source for directing light via at least a portion of the detection path in a reverse direction to the sample for aligning, sample presence detection, localizing, and/or focusing based on analysis of the resulting illumination spot on the sample.

In one design, the source of radiation is a laser, the optical emission path includes an apertured mirror and a focusing lens, and the detection path includes the focusing lens and the apertured mirror. The system may further include a camera aimed at the sample for viewing the resulting illumination spot on the sample.

Also featured is a handheld LIBS spectrometer system. An optic stage is moveable with respect to the device housing and includes a laser focusing lens. A laser source is mounted in the housing for directing a laser beam to a sample via the laser focusing lens. A detection fiber bundle is mounted in the housing. A first mirror is located between the laser source and the focusing lens and includes an aperture for the laser beam. The apertured mirror is oriented to redirect plasma radiation passing through the focusing lens for delivery to the detection fiber bundle. A spectrometer subsystem in the housing receives plasma radiation via the detection fiber bundle. At least one fiber of the fiber bundle connected to a source of illumination for directing light via the mirror and the focusing lens to the sample for alignment, sample presence detection, localization, and/or focusing of the laser beam. The LIBS spectrometer system may further include a camera aimed at the sample for viewing illumination on the sample.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIG. 7 is a gray scale intensity map showing an image peak of reflected radiation from a clear glass sample;

FIG. 8 is a gray scale intensity map showing the lack of a discernable peak when no sample was present and the LED was energized;

DETAILED DESCRIPTION OF THE INVENTION

Figure 1:
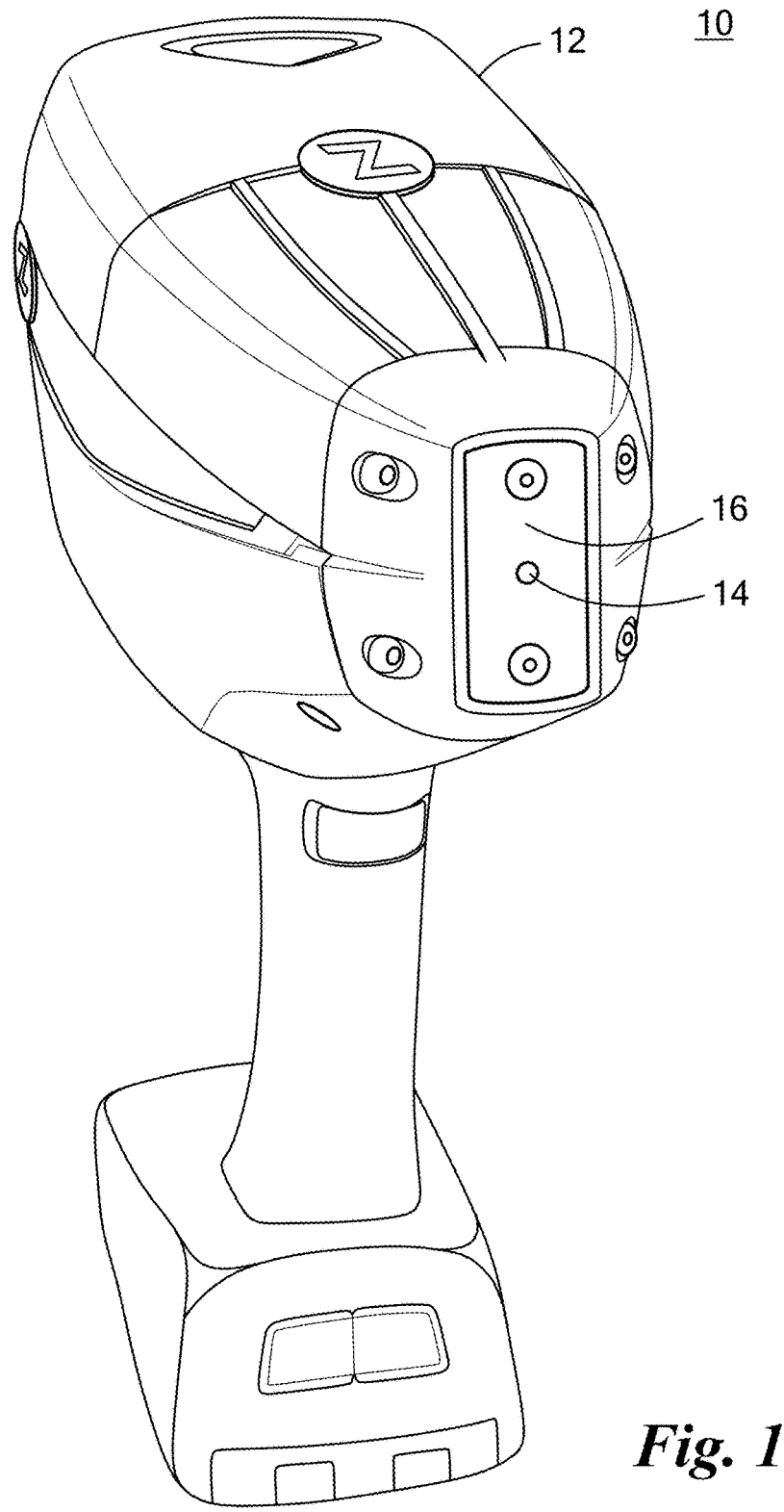
FIG. 1 is a schematic view showing an example of a handheld LIBS analyzer in accordance with aspects of the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 2:
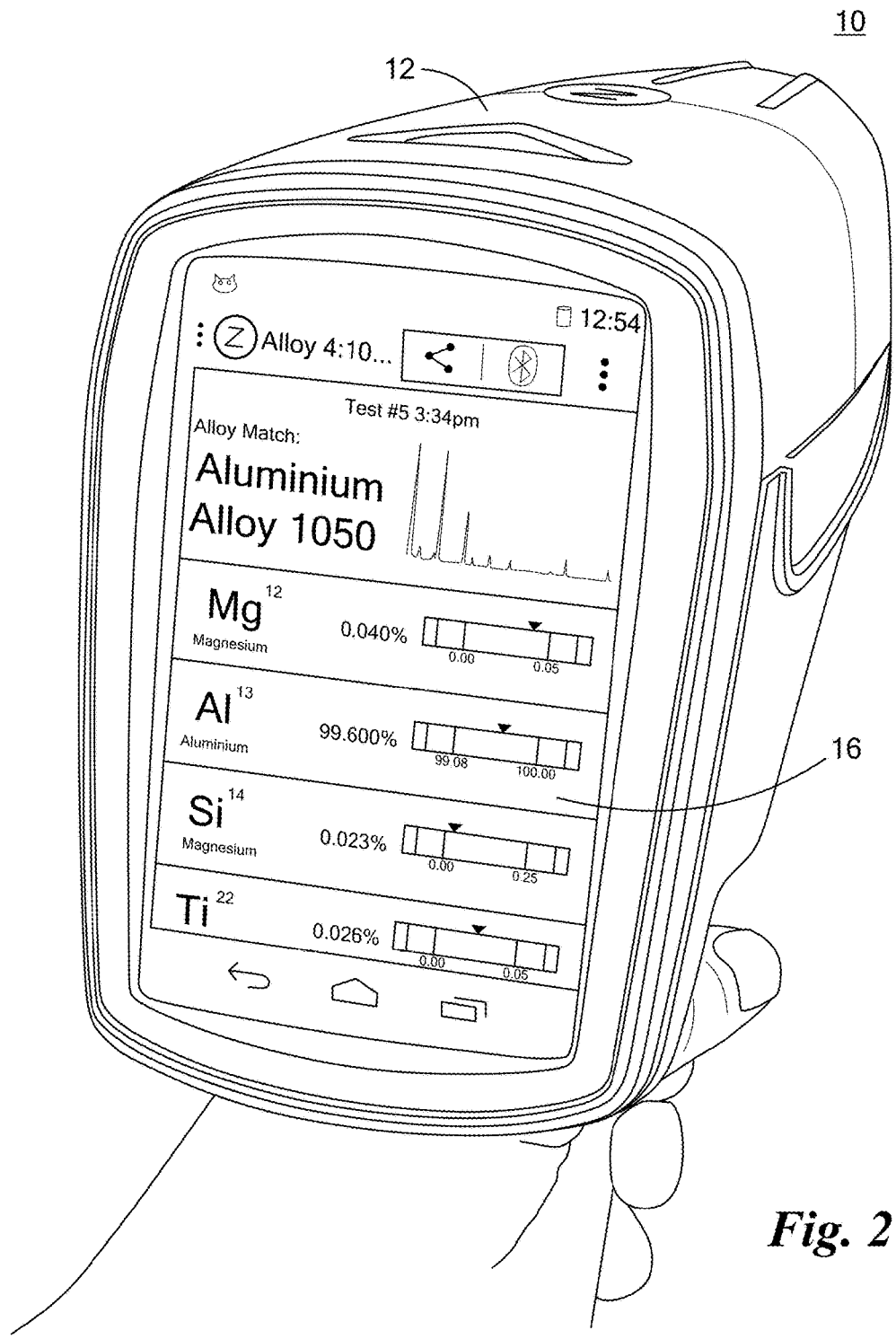
FIG. 2 is a schematic rear view showing the display screen of the handheld LIBS analyzer of FIG. 1.

FIG. 1 shows a handheld LIBS analyzer 10 with housing 12 enclosing a laser, spectrometers, optics, optical stages, processors and the like as discussed below. The laser exits orifice 14 in end plate 16. The resulting plasma created on a sample abutting end plate 16 is automatically analyzed and the results are displayed on screen 16, FIG. 2. See co-pending U.S. patent application Ser. No. 14/874,726.

Figure 3:
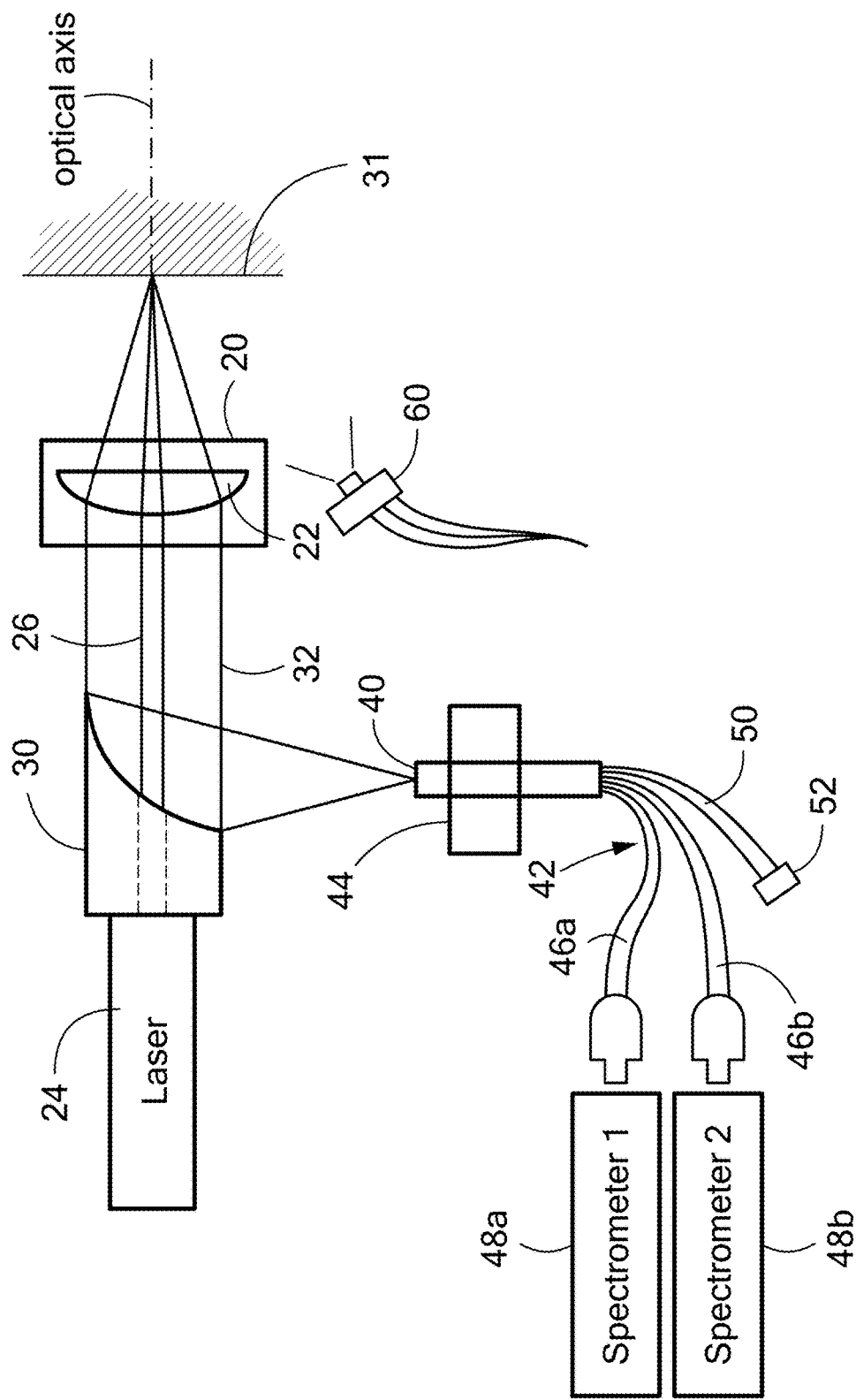
FIG. 3 is a schematic block diagram showing the primary components associated with a handheld LIBS analyzer in accordance with the invention.

In one exemplary design, optic stage 20, FIG. 3 is movable with respect to the instrument housing and includes laser focusing lens 22. Laser source 24 mounted in the housing directs a laser beam 26 along the optical axis to a sample through an apertured off axis parabolic mirror 30 to adjustable focusing lens 22 and then to sample 31. Plasma radiation 32 is directed through focusing lens 22 and to the common end 40 of the fiber optic bundle 42 via mirror 30. Common end 40 of fiber optic bundle 42 is mounted within the instrument housing using an adjustable alignment mount or clamp 44. One or more branches 46a, 46b of the fiber optic bundle are connected to a spectrometer subsystem such as spectrometers 48a, 48b, respectively. Each branch preferably includes multiple fibers but may, in some designs, only include one fiber. Additional spectrometers and branches are possible.

One fiber (or one bundle) 50 is connected to a source of illumination such as LED 52. Here, the emission path is from the laser to the sample (via the aperture in mirror 30 and focusing lens 22) and the detection path is from the sample to the spectrometer(s) (via focusing lens 22, mirror 30, and fiber optic bundle 42). A portion of the detection path thus is concentric with a portion of the emission path. So, light from LED 52 proceeds along a portion of detection path in a reverse direction to the sample. Light reflected off the sample when LED 52 is energized proceeds along a portion of the detection path to the common end of the fiber optic bundle and then to the spectrometer subsystem. In this way, by analyzing the resulting spot of light on the sample, various functions can be carried out, including, but not limited to, alignment, sample presence detection, analysis localization, and laser beam focusing.

Video camera 60 within the device housing can be used to image the resulting illumination spot on sample 31. In testing, with LED 52 energized, an illumination spot was clearly seen using camera 60 on black tape, a paper towel, a dark rock, and an aluminum sample.

The specific design of FIG. 3 can be varied as shown in FIGS. 36-38 and 40-41 of co-pending U.S. patent application Ser. No. 14/874,726. A camera is shown in that application in FIG. 42. Also, the techniques disclosed herein may be applicable to other analyzers. For example, the radiation source may be a low power continuous wave laser source for Raman analysis.

The illumination spot on the sample may be used to align common end 40 of fiber bundle 42 during manufacturing or final testing of the unit. In one example, the laser 24 is fired creating a mark on the sample. For example, a visible crater in a test sample can be imaged by camera 60 and displayed on screen 16, FIG. 2. The LED 52 is then energized creating a focused spot of illumination on the sample. Common end 40 of the fiber bundle 42 is then adjusted using mount or clamp 44 until the illumination spot is concentric with the crater formed in the sample. Common end 40 of the fiber bundle is moved left and right, for example, in FIG. 3 until concentricity is achieved and then the common end is fixed at that location.

Also, the laser can be focused onto the sample using adjustable focusing lens 22. Then, the common end 40 of the fiber bundle 42 is moved closer and further away from mirror 30 while LED 50 is energized until the smallest illumination spot possible is imaged on the sample. Then, the alignment mount or clamp 44 is tightened. Now, the alignment of the fiber bundle common end with the laser beam location on the sample is optimized for enhanced plasma radiation collection.

In another example, a translucent tape is placed across end plate 16, FIG. 1 and laser 24, FIG. 3 is energized to create a hole through the tape. LED 52 is energized and common end 40 is adjusted using mount 44 until the illumination spot on the tape is concentric with the hole therein and the illumination spot size is minimized as viewed from the outside or via a camera.

The illumination spot may also be used to detect the presence of a sample abutting or proximate end plate 16, FIG. 1 for safety. If a sample is present, the illumination spot reflected off the sample can be detected by camera 60, FIG. 3 and/or by one or more spectrometers 48. If no illumination spot is detected, the laser 24 may be locked out by one or more controllers of the system or the laser beam 26 may be automatically blocked in some fashion to prevent injury if the laser beam were to proceed through the air. A threshold level of illumination, if not detected, may also be used to lock out the laser.

Figure 4:
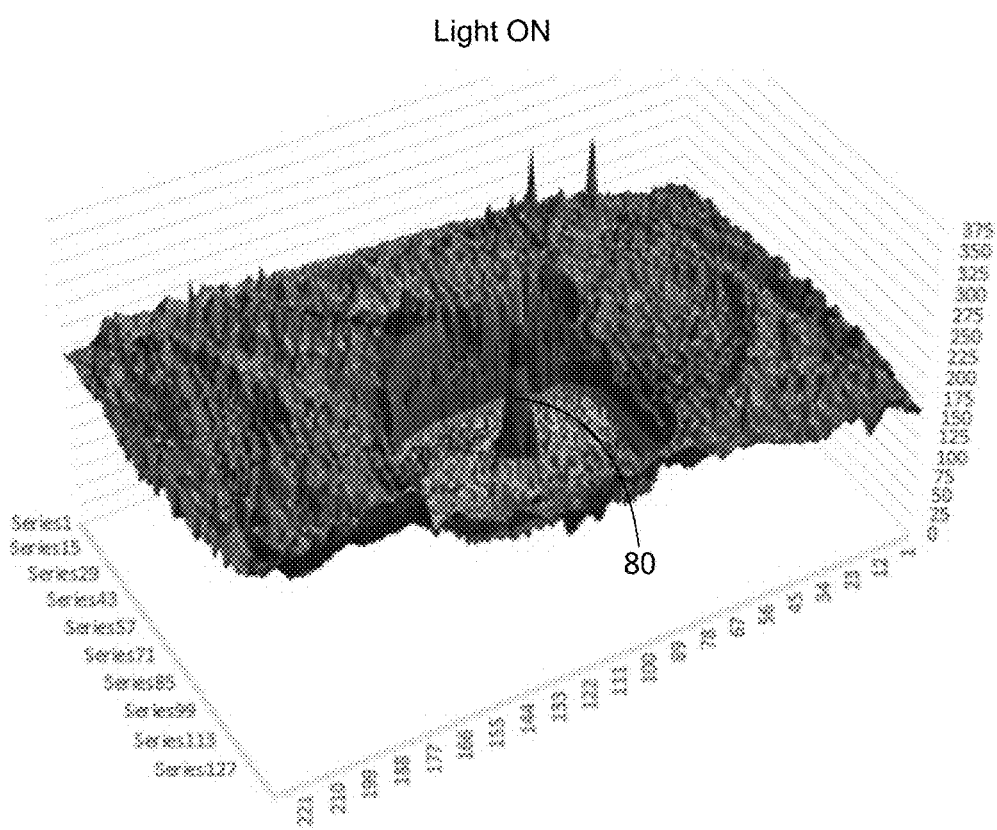
FIG. 4 is a gray scale intensity map of reflected radiation imaged by a camera when the LED of FIG. 3 was energized to provide an illumination spot on a black tape adhesive sample.
Figure 5:
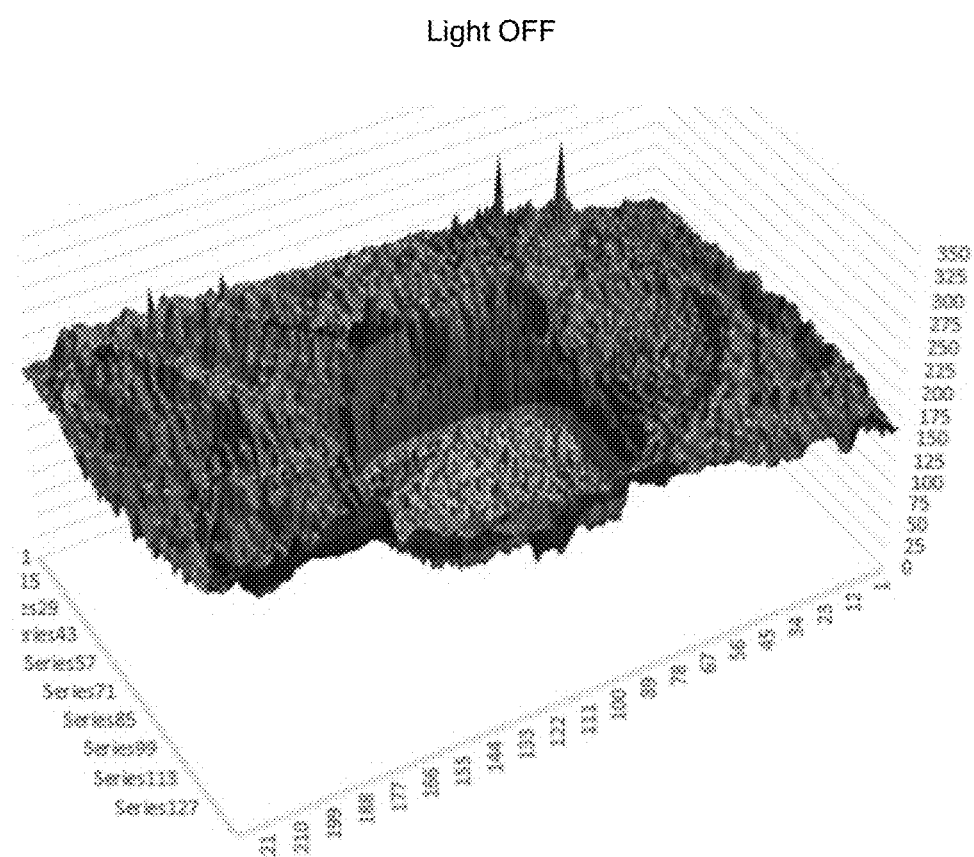
FIG. 5 is a gray scale intensity map of the same sample when the LED was de-energized.
Figure 6:
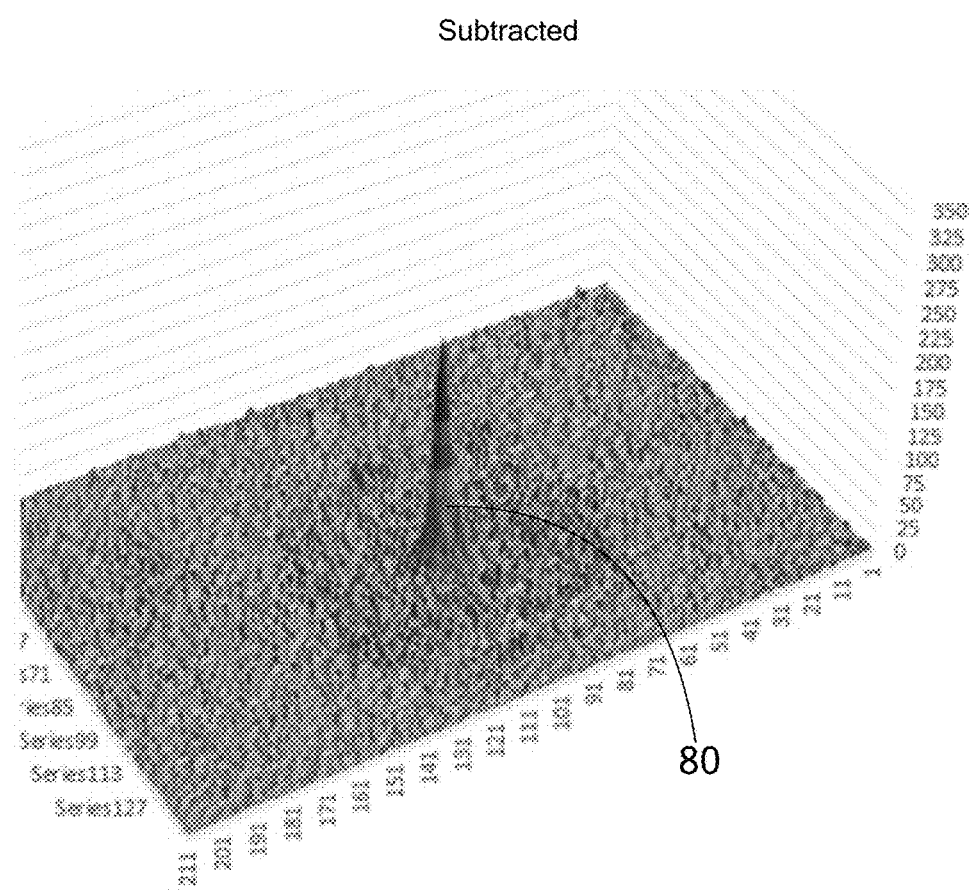
FIG. 6 is a gray scale intensity map resulting from the subtraction of the data shown in FIG. 5 from the data shown in FIG. 4.

To account for noise, the sample may be imaged or spectral data from the spectrometer(s) collected both with the LED 52 energized and de-energized. The analyzed radiation when the LED 52 is de-energized may thus be subtracted from the analyzed radiation when the LED 52 is energized. FIGS. 4-6, for example, are gray scale intensity maps of radiation reflected off a flat black sample surface imaged by camera 60, FIG. 3 with the LED energized (FIG. 4) de-energized (FIG. 5) and these two results subtracted (FIG. 6). Radiation reflected off the sample due to the LED being energized is shown at 80 in FIGS. 4 and 6. A similar result, but with a smaller peak 82, FIG. 7 was obtained on a glass sample.

FIG. 8 shows the result with no sample present. No peak at all is present when the LED was energized, de-energized, and the results subtracted. Clear glass is perhaps the most difficult sample to detect. Moreover, a threshold level of radiation being detected may be used to prevent clear materials from being allowed to activate the laser.

In other examples, during argon pre-purge or possibly before every laser pulse, the LED can be modulated on and off at a predetermined frequency. The video camera can be used or alternatively spectra can be collected using the spectrometer(s) in both the on and off states. For video analysis, two images from the on and off states are subtracted and if the difference yields a spot above a certain threshold, the sample is determined to be present. The laser is then allowed to fire. For spectroanalysis, a spectrum may be taken for the on and off states of the LED and the two spectra subtracted. The wavelength region in the vicinity of the LED wavelength may be integrated and if the result is above a predetermined threshold, the sample may be determined to be present and the laser allowed to be fired. Another possibility is to modulate the energizing of the LED (e.g., at approximately a kilohertz) and simultaneously collect data from a photodiode located near the nose of the device. A Fourier transform of the resulting signal would be sensitive to the modulated signal with a high background of other light. A synchronous detection scheme may also be used.

Figure 9:
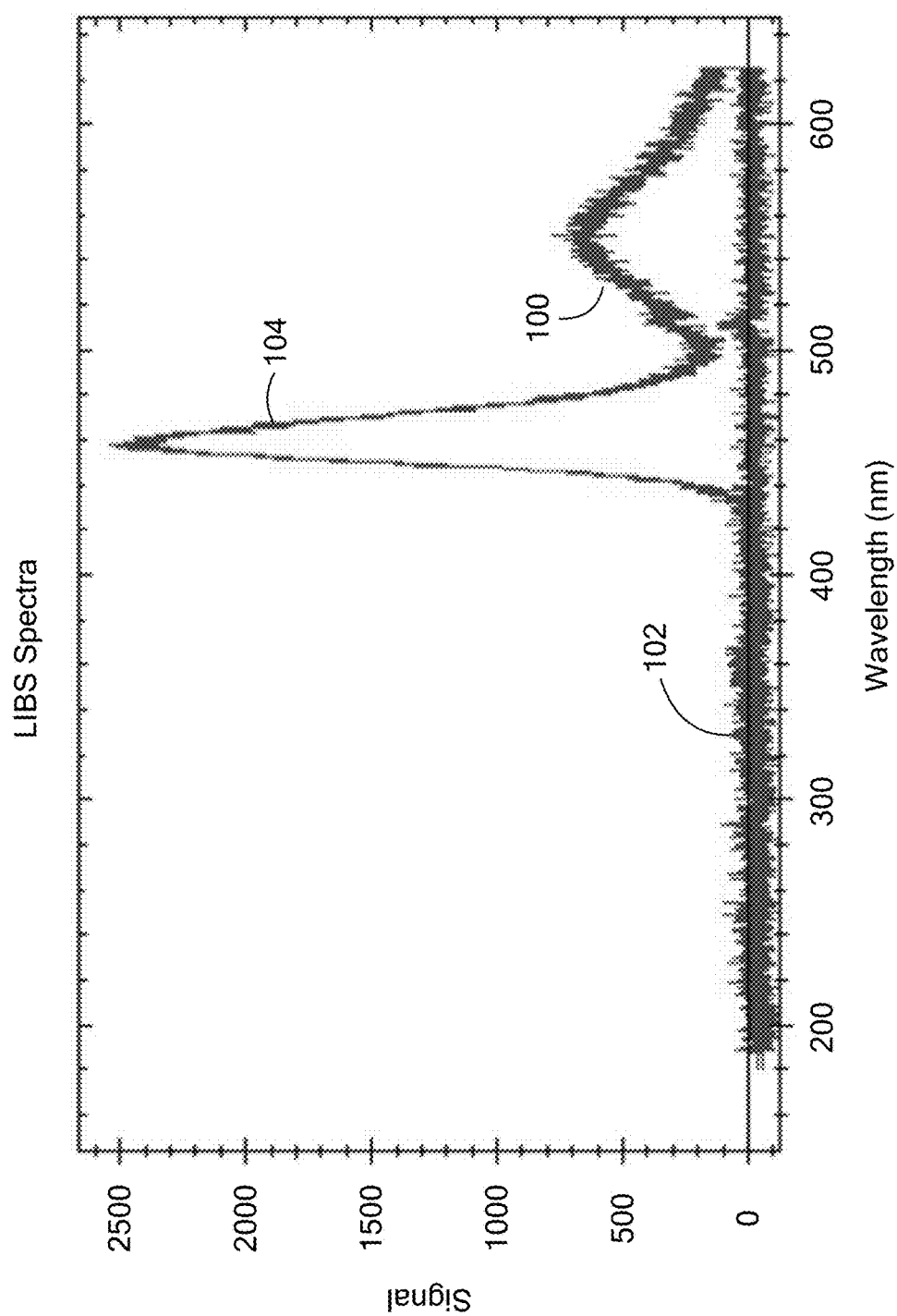
FIG. 9 is spectrum produced by the spectrometer subsystem of the illumination spot on white paper compared to the spectrum when illumination spot was not present on the white paper.

High speed sample presence detection can be accomplished by energizing LED 52, FIG. 3 which may be three color LED (e.g., blue, green, yellow). The laser is not fired. A measurement is made using one or more spectrometers 48a, 48b as shown at 100 in FIG. 9. The LED is then de-energized and another spectrometer measurement is made as shown at 102 in FIG. 9. The resulting two spectra are then subtracted and an LED emission band is analyzed as shown at 104. Each scan took 64 milliseconds.

Figure 10A:
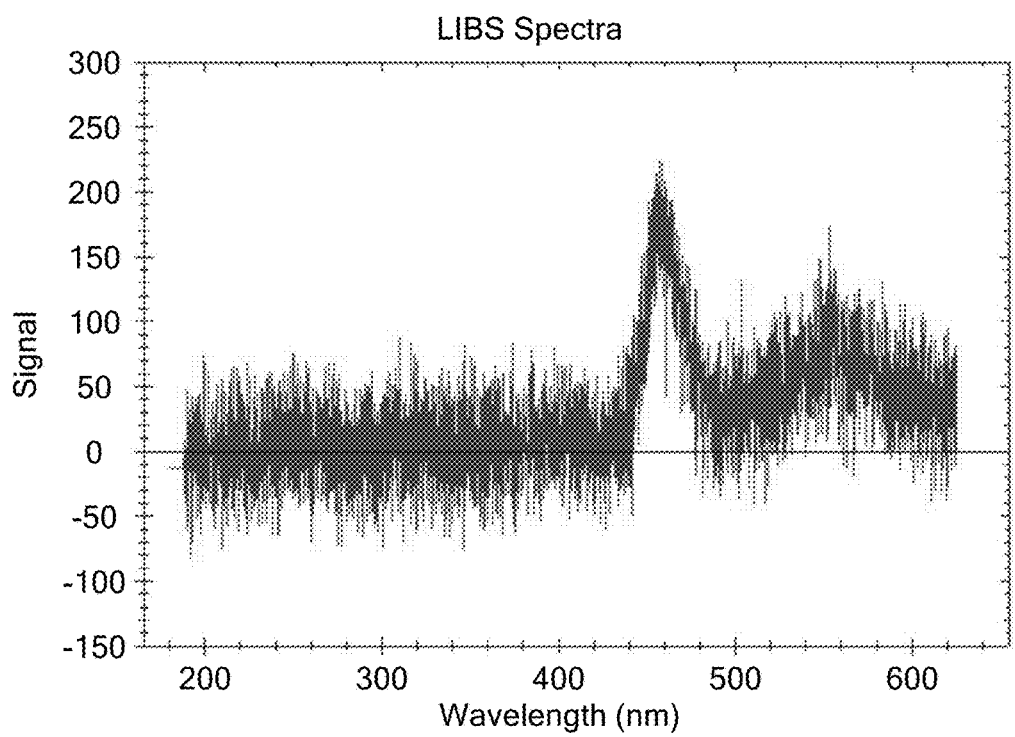
FIG. 10A is an output of the spectrometer subsystem when a supplemental light was also used to illuminate a sample.
Figure 10B:
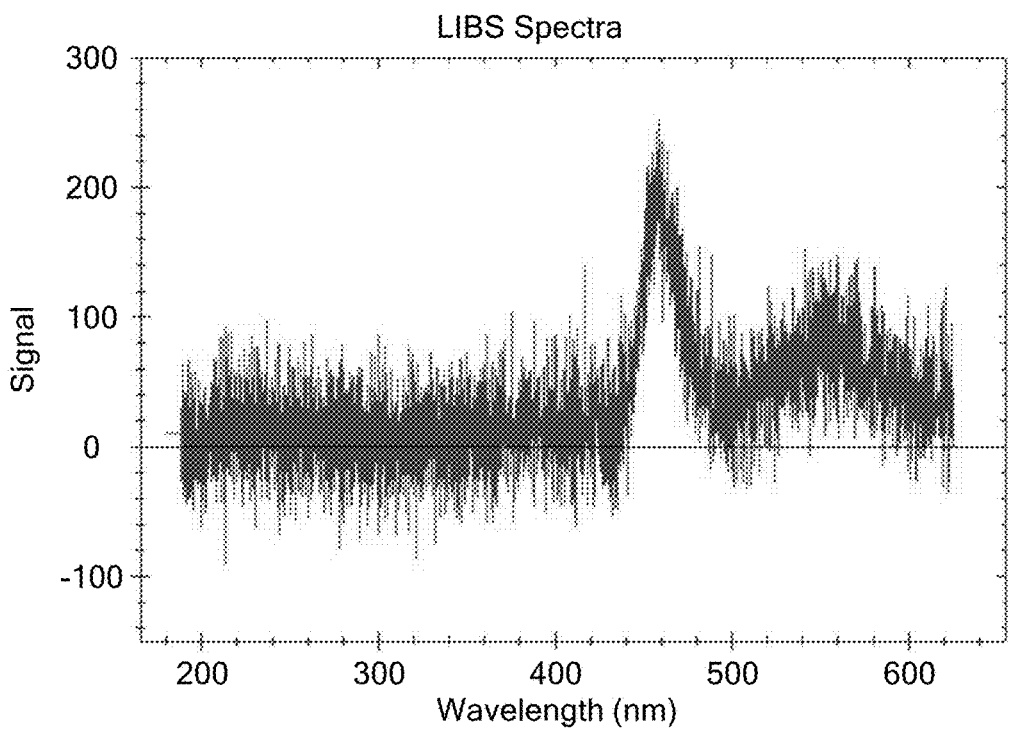
FIG. 10B shows the spectrum produced when the supplemental light was turned off.
Figure 11:
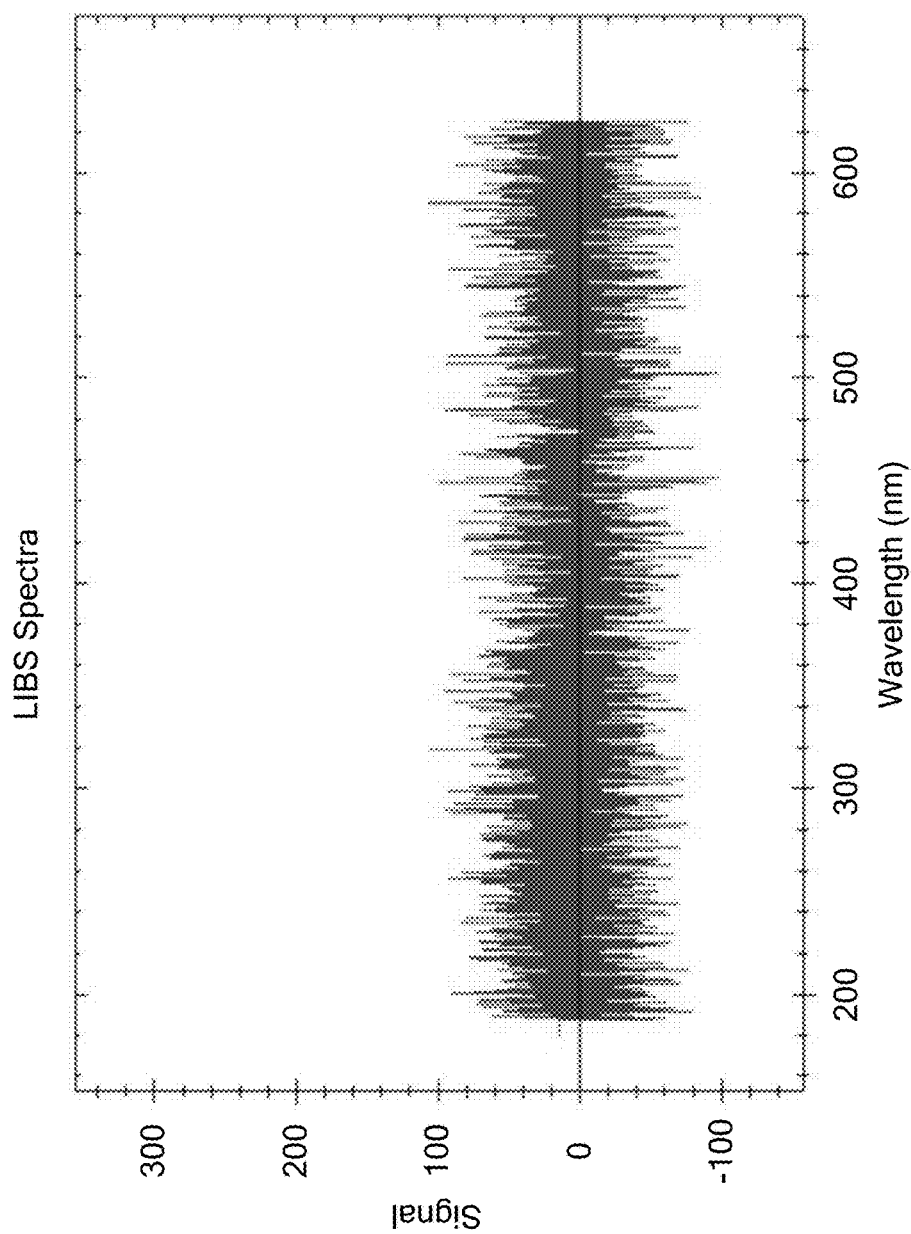
FIG. 11 shows the spectrum produced with no sample present with both the supplemental illumination turned on and off.

Even if the sample is illuminated by another source such as a light on the handheld LIBS analyzer, the presence or absence of a sample can be readily detected using the spectrometer subsystem as shown in FIGS. 10A and 10B. In FIG. 10A, the other illumination source was turned on and in FIG. 10B the other illumination source was turned off. In both cases, the LED illumination spot on the sample could be detected as shown at the peak at about 450 nm. With no sample present with both the separate illumination source turned on and off, no discernable peak was detected as shown in FIG. 11.

Figure 12A:
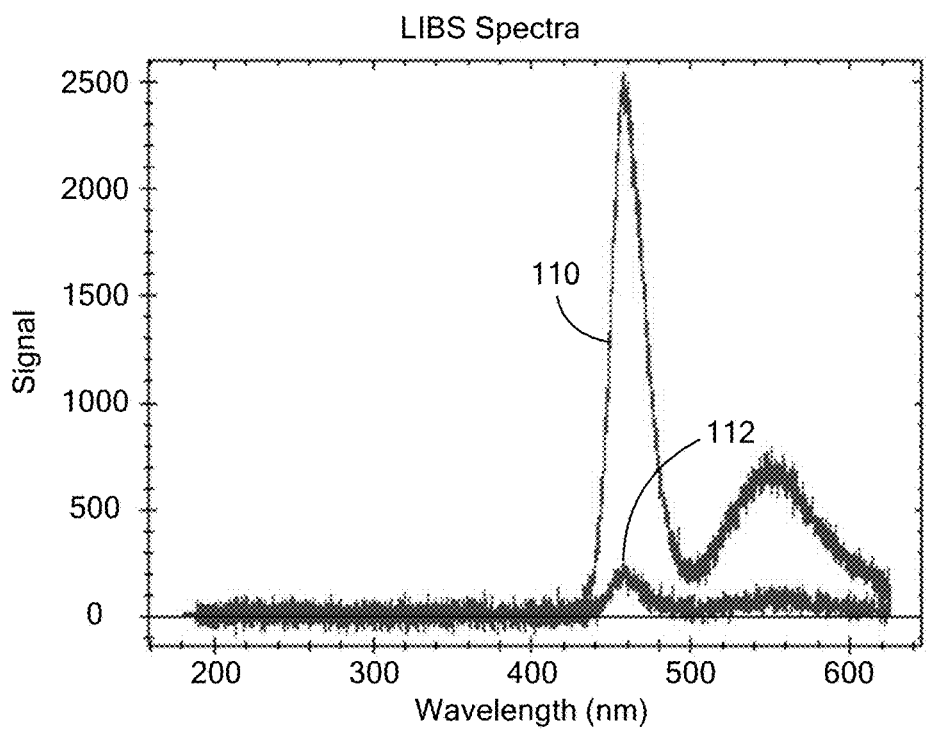
FIG. 12A is a comparison of the spectrum produced by the LED illumination source comparing the HQI of a dark rock with a white paper reference.
Figure 12B:
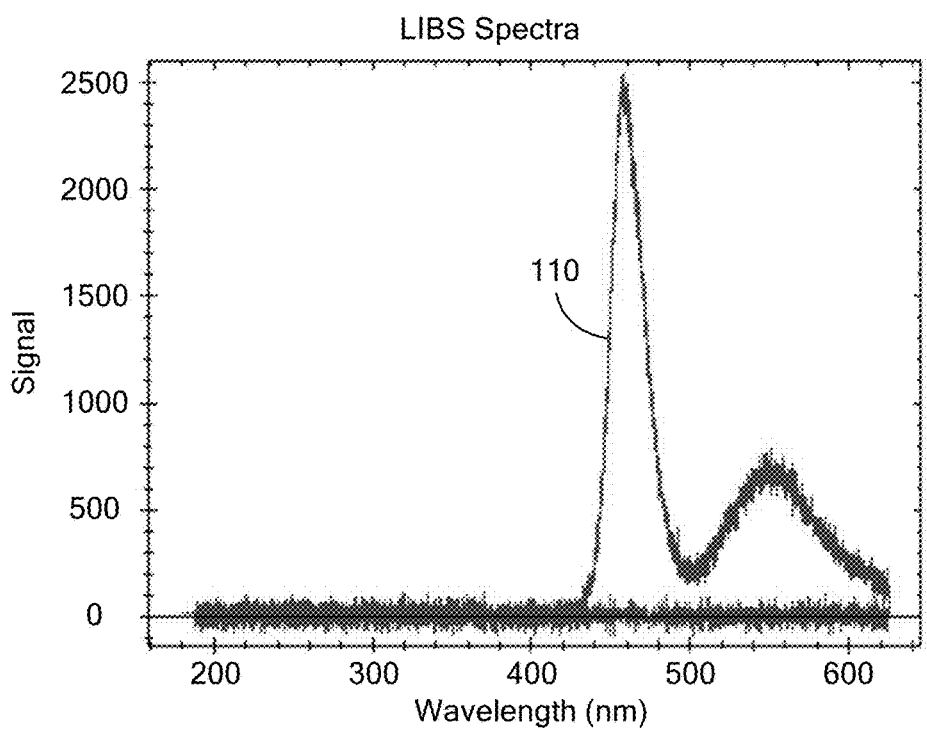
FIG. 12B is the same white paper reference compared to a situation where no sample was present and the LED illumination source was energized.

A hit quality index technique can be used as shown in FIGS. 12A and 12B where the reference stored in memory including a library onboard the handheld LIBS analyzer was based on a white paper illuminated by the LED as shown at 110. A dark rock sample as shown at 112 produced an HQI factor of 0.915 (FIG. 12A) while no sample present produced a HQI factor of only 0.104 as shown in FIG. 12B.

The one or more spectrometers can be used to detect sample presence with good HQI results even for dark rock. The measurement time was around 128 msec but could be faster and could offer a faster analysis method than camera (e.g., video) analysis depending on how fast the processing subsystem of the apparatus can capture and process two frames. Spectrometer or video analysis can be carried out at the start of a measurement before the laser is fired. During measurement when the laser is fired, an alternative method can be used to detect if the sample is still present or has been removed. See co-pending U.S. patent application Ser. No. 14/800,888 filed Jul. 16, 2015 and U.S. application Ser. No. 14/632,419 filed Feb. 26, 2015 both incorporated herein by this reference.

To analyze a specific location on the sample, LED 52 can be energized and focusing lens 22 adjusted in a direction normal to the optical axis (using software controls) via X, Y, and Z stage 20 to translate the illumination spot to the desired sample location. The location of the illumination spot will be displayed on screen 16, FIG. 2, for example, which is an output of camera 60, FIG. 3. Then, when laser 24 is energized, the laser beam will strike the sample at that specific location. In another example, the LED can be energized creating an illumination spot on the sample and the sample then moved until the illumination spot is at the desired location on the sample.

Also, the illumination spot can be used to focus the laser beam precisely on the sample. LED 52 is energized and focusing lens 22 is adjusted along the optical axis until the size of the illumination spot on the sample is minimized. At that position of the focusing lens, the laser beam will now be focused on the sample. This process may be automated by software controlling one or more controllers of the system. Subtracting radiation data received during the focusing cycle while the LED is de-energized from radiation data received while the LED is energized may be used to improve the signal to noise ratio. Full width at half maximum techniques may be used. The one or more spectrometers could also be used to determine the illumination spot size on the sample where, for example, the brightest spot is determined to be the smallest. This focusing cycle may be automated and performed each time the laser is fired, between successive pulse trains of the laser, and/or each time the unit is turned on.

Accordingly, the LED 52, FIG. 3 (or other light source) can be used to perform various functions in a LIBS or other spectroscopic system.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. An analysis method comprising:
   directing a laser beam from a source of radiation along an emission path to create a mark on a sample;
   directing photons emitted by the sample along a detection path including a detection fiber bundle having a common end located to receive said photons emitted by the sample;
   directing light from an illumination source coupled to a fiber of the fiber bundle via at least a portion of the detection path to the sample creating an illumination spot thereon; and
   analyzing the illumination spot on the sample for aligning the position of the detection fiber bundle common end based on the illumination spot by adjusting the position of the detection fiber bundle common end until the illumination spot is concentric with the mark created on the sample.

2. The method of claim 1 in which aligning further includes focusing the laser beam on the sample by adjusting the position of the fiber bundle common end until the size of the illumination spot is minimized.

3. The method of claim 1 in which the sample is a tape and the mark is a hole created through the tape.

4. The method of claim 1 in which the sample includes a substrate and the mark is a crater in the substrate.

\* \* \* \* \*